(12) United States Patent
Jugl et al.

(10) Patent No.: US 10,159,801 B2
(45) Date of Patent: Dec. 25, 2018

(54) ASSEMBLY FOR A DRUG DELIVERY DEVICE AND DRUG DELIVERY DEVICE

(71) Applicant: Sanofi-Aventis Deutschland GMBH, Frankfurt am Main (DE)

(72) Inventors: Michael Jugl, Frankfurt am Main (DE); Axel Teucher, Frankfurt am Main (DE); Marc Holtwick, Frankfurt am Main (DE)

(73) Assignee: Sanofi-Aventis Deutschland GMBH, Frankfult am Main (DE)

( * ) Notice: Subject to any disclaimer, the term of this patent is extended or adjusted under 35 U.S.C. 154(b) by 22 days.

(21) Appl. No.: 15/105,738

(22) PCT Filed: Dec. 18, 2014

(86) PCT No.: PCT/EP2014/078415
§ 371 (c)(1),
(2) Date: Jun. 17, 2016

(87) PCT Pub. No.: WO2015/091763
PCT Pub. Date: Jun. 25, 2015

(65) Prior Publication Data
US 2016/0317753 A1 Nov. 3, 2016

(30) Foreign Application Priority Data
Dec. 20, 2013 (EP) .................................... 13198704

(51) Int. Cl.
*A61M 5/315* (2006.01)
*A61M 5/20* (2006.01)
(Continued)

(52) U.S. Cl.
CPC .......... *A61M 5/31585* (2013.01); *A61M 5/20* (2013.01); *A61M 5/2033* (2013.01);
(Continued)

(58) Field of Classification Search
CPC .. A61M 5/31513; A61M 5/2033; A61M 5/20; A61M 5/31583; A61M 5/482; A61M 2005/2086
See application file for complete search history.

(56) References Cited

U.S. PATENT DOCUMENTS

| | | | |
|---|---|---|---|
| 533,575 A | 2/1895 | Wilkens | |
| 4,865,591 A | 9/1989 | Sams | |

(Continued)

FOREIGN PATENT DOCUMENTS

| | | |
|---|---|---|
| CA | 2138528 | 2/1994 |
| CA | 2359375 | 7/2000 |

(Continued)

OTHER PUBLICATIONS

International Search Report and Written Opinion in International Application No. PCT/EP2014/078415, dated Apr. 17, 2015, 10 pages.

(Continued)

*Primary Examiner* — Bradley J Osinski
(74) *Attorney, Agent, or Firm* — Fish & Richardson P.C.

(57) ABSTRACT

Assembly for a drug delivery device and drug delivery device An assembly for a drug delivery device (1) is described comprising an activation member (6A) adapted and arranged to be axially moved in a delivery direction for triggering a dose delivery operation of the assembly, a first interaction member (17) and a second interaction member (18) which are adapted and arranged to mechanically cooperate with one another during a dose delivery operation of the assembly and to be rotated with respect to one another during the dose delivery operation, wherein the assembly is configured such that movement of the activation member (6A) in the delivery direction brings the interaction members (17, 18) into mechanical contact for generating a friction between the interaction members (17, 18), wherein an (Continued)

amount of friction controls a relative rotational speed of the interaction members (17, 18) during a dose delivery operation. Furthermore, a drug delivery device comprising the assembly is described.

26 Claims, 2 Drawing Sheets (51) Int. Cl.
*A61M 5/24* (2006.01)
*A61M 5/48* (2006.01)
(52) U.S. Cl.
CPC .......... *A61M 5/24* (2013.01); *A61M 5/31553* (2013.01); *A61M 5/31583* (2013.01); *A61M 5/482* (2013.01); *A61M 2005/2086* (2013.01)

(56) References Cited

U.S. PATENT DOCUMENTS

| | | |
|---|---|---|
| 5,092,842 A | 3/1992 | Bechtold |
| 5,226,895 A | 7/1993 | Harris |
| 5,226,896 A | 7/1993 | Harris |
| 5,279,586 A | 1/1994 | Balkwill |
| 5,304,152 A | 4/1994 | Sams |
| 5,320,609 A | 6/1994 | Haber et al. |
| 5,378,233 A | 1/1995 | Haber |
| 5,383,865 A | 1/1995 | Michel |
| 5,391,157 A | 2/1995 | Harris |
| 5,480,387 A | 1/1996 | Gabriel et al. |
| 5,505,704 A | 4/1996 | Pawelka et al. |
| 5,582,598 A | 12/1996 | Chanoch |
| 5,626,566 A | 5/1997 | Petersen et al. |
| 5,674,204 A | 10/1997 | Chanoch |
| 5,688,251 A | 11/1997 | Chanoch |
| 5,807,346 A | 9/1998 | Frezza |
| 5,820,602 A | 10/1998 | Kovelman |
| 5,851,079 A | 12/1998 | Horstman |
| 5,921,966 A | 7/1999 | Bendek et al. |
| 5,961,495 A | 10/1999 | Walters et al. |
| 6,004,297 A | 12/1999 | Steenfeldt-Jensen et al. |
| 6,193,698 B1 | 2/2001 | Kirchhofer et al. |
| 6,221,046 B1 | 4/2001 | Burroughs et al. |
| 6,235,004 B1 | 5/2001 | Steenfeldt-Jensen et al. |
| 6,248,095 B1 | 6/2001 | Giambattista et al. |
| 6,562,006 B1 | 5/2003 | Hjertman |
| 6,613,023 B2 | 9/2003 | Kirchhofer |
| 6,699,224 B2 | 3/2004 | Kirchhofer |
| 6,932,794 B2 | 8/2005 | Giambattista |
| 6,936,032 B1 | 8/2005 | Bush, Jr. et al. |
| 7,169,132 B2 | 1/2007 | Bendek |
| 7,241,278 B2 | 7/2007 | Moller |
| 7,678,084 B2 | 3/2010 | Judson |
| 8,187,233 B2 | 5/2012 | Harms et al. |
| 9,802,001 B2 * | 10/2017 | Higgins ................. A61M 5/20 |
| 2002/0052578 A1 | 5/2002 | Moller |
| 2002/0120235 A1 | 8/2002 | Enggaard |
| 2003/0050609 A1 | 3/2003 | Sams |
| 2004/0059299 A1 | 3/2004 | Moller |
| 2004/0097883 A1 | 5/2004 | Roe |
| 2004/0210199 A1 | 10/2004 | Atterbury et al. |
| 2004/0267207 A1 | 12/2004 | Veasey et al. |
| 2005/0113765 A1 | 5/2005 | Veasey et al. |
| 2006/0153693 A1 | 7/2006 | Fiechter et al. |
| 2007/0016143 A1 | 1/2007 | Miller et al. |
| 2008/0306446 A1 | 12/2008 | Markussen |
| 2009/0275916 A1 | 11/2009 | Harms et al. |
| 2010/0114038 A1 * | 5/2010 | Sams ................. A61M 5/2033 604/211 |
| 2011/0077595 A1 | 3/2011 | Eich et al. |

FOREIGN PATENT DOCUMENTS

| | | |
|---|---|---|
| EP | 0496141 | 7/1992 |
| EP | 0897729 | 2/1999 |
| EP | 0937471 | 8/1999 |
| EP | 0937476 | 8/1999 |
| EP | 1776975 | 4/2007 |
| GB | 0304822.0 | 3/2003 |
| GB | 0304823.8 | 11/2017 |
| WO | WO 93/07922 | 4/1993 |
| WO | WO 93/24160 | 12/1993 |
| WO | WO 1999/038554 | 8/1999 |
| WO | WO 2001/010484 | 2/2001 |
| WO | WO 02/030495 | 4/2002 |
| WO | WO 02/092153 | 11/2002 |
| WO | WO 03/080160 | 10/2003 |
| WO | WO 2006/084876 | 8/2006 |
| WO | WO2008/053243 | 5/2008 |
| WO | WO2009/098502 | 8/2009 |
| WO | WO2011/043605 | 4/2011 |

OTHER PUBLICATIONS

International Preliminary Report on Patentability in International Application No. PCT/EP2014/078415, dated Jun. 21, 2016, 8 pages.
Rote Liste, "50. Hypophysen-, Hypothalamushormone, andere regulatorische Peptide u. ihre Hemmstoffe," Chapter 50, ed. 2008, 20 pages.
"Pen-injectors for medical use—Part 1: Pen-injectors—Requirements and test methods," International Standard, reference No. ISO 11608-1:2000(E), first edition Dec. 15, 2000, 32 pages.

* cited by examiner

ASSEMBLY FOR A DRUG DELIVERY DEVICE AND DRUG DELIVERY DEVICE

CROSS-REFERENCE TO RELATED APPLICATIONS

This application is a U.S. national stage application under 35 USC § 371 of International Application No. PCT/EP2014/078415, filed on Dec. 18, 2014, which claims priority to European Patent Application No. 13198704.2, filed on Dec. 20, 2013, the entire contents of which are incorporated herein by reference.

The present disclosure relates to an assembly for a drug delivery device. The present disclosure further relates to a drug delivery device. In particular, the disclosure relates to pen-type drug delivery devices.

Pen-type drug delivery devices are used for injections by persons without formal medical training. This is increasingly common for self-treatment among patients having diabetes or the like. By means of a drive mechanism, a bung in a cartridge is displaced such that a drug accommodated in the cartridge is dispensed through a needle.

Prior to injection, the required dose of the drug is set by means of a dose setting mechanism. Common designs of dose setting mechanisms comprise a number of tubular or sleeve-like elements such as a dose setting sleeve, a dose indicating sleeve, a drive sleeve and/or a ratchet sleeve. Such sleeves are often accommodated within and connected to each other. Some devices comprise a power assist, in particular an energy storing member, wherein energy may be stored in the energy storing member during the setting of a dose. This energy may be released during dose delivery.

A power assisted drug delivery device is described in document US 2008/0306446 A1, for example.

Power assisted drug delivery devices are beneficial, in particular when the injection of larger volumes and/or highly viscous fluids is intended. The energy storing member must have a force profile sufficient to enable delivery of the entire dose. This has the impact that at least small doses are dispensed with high force and, therefore, in a fast manner. Fast injections may lead to user discomfort, as the injected tissue is stressed and the user may even feel pain.

Certain aspects of the present invention relate to a drug delivery device having improved properties, e.g. increased user comfort.

One aspect relates to an assembly for a drug delivery device. The assembly may comprise a drive mechanism of the device. A drive mechanism may be a mechanism adapted for setting and/or dispensing a dose of drug from the device. The assembly may comprise an activation member. The activation member may be adapted and arranged to be moved in a delivery direction for triggering a dose delivery operation of the assembly. The activation member may be axially moveable in the delivery direction. The activation member may be prevented from being rotated or tilted when being moved in the delivery direction. The activation member may be prevented from being moved in a radial direction with respect to a main longitudinal axis of the assembly and, thus, of the device for delivering a dose of the drug. By means of moving the activation member at least partly in the delivery direction, a dose delivery operation may be started. The activation member may comprise a dose button, for example.

The assembly may further comprise a first interaction member. The assembly may comprise a second interaction member. The interaction members may be adapted and arranged to mechanically cooperate with one another during a dose delivery operation of the assembly. Furthermore, the interaction members may be adapted and arranged to be rotated with respect to one another during the dose delivery operation. The interaction members may also be adapted and arranged to be axially displaced with respect to one another during the dose delivery operation.

The assembly may be configured such that movement of the activation member in the delivery direction brings the interaction members into mechanical contact for generating a friction between the interaction members. An amount of friction may control a relative rotational speed of the interaction members during a dose delivery operation. By means of controlling the friction between the interaction members during dose delivery, a user can influence the relative rotational speed between the interaction members and, thus, an injection speed of the assembly. In particular, the interaction members function as a break of the assembly and, thus, of the device. The speed can be adjusted to the individual needs of the user. For example, the speed can be determined by which drug is to be delivered from the device. In this way, provision of a drug delivery device with high user comfort is facilitated.

According to one embodiment, the activation member is configured to be pushed in the delivery direction by a user. The distance, in particular the axial distance, by which the activation member is pushed in the delivery direction may be adjustable. In particular, the distance may be influenceable by the user. The assembly may be configured such that an amount of pressure exerted onto the activation member determines the amount of friction generated between the interaction members. The more the activation member may be pushed in the delivery direction, the more friction may be generated between the interaction members. Thus, by controlling the force exerted onto the activation member and, thus, the distance by which the activation member is moved in the delivery direction, the user can easily control the injection speed. Hence, provision of a easily working and user friendly device is facilitated.

According to one embodiment, the activation member is adapted and arranged to be moved in the delivery direction by a first distance. A length of the first distance may be variable. The length of the first distance may depend on an outer shape of the interaction members, for example. The activation member may be adapted and arranged to be moved by the first distance from a first position into a second position. The first position may be a fixed position, e.g. the starting position. The second position may be a variable position. When the activation member is moved by the first distance, the interaction members may be free from mechanical cooperation. Accordingly, the activation member may be moveable at least partly in the delivery direction without generating a friction between the interaction members. In this way, the user may achieve a dose delivery operation at full speed, in particular without influencing the injection speed. In this way, provision of a drug delivery device with high user comfort is facilitated.

According to one embodiment, the activation member is adapted and arranged to be moved in the delivery direction by a second distance. The activation member may be adapted and arranged to be moved by the second distance from the second position into a third position. Both, the second and the third positions may be variable positions, e.g. positions depending on a structure of the components of the assembly. Alternatively, only the second position may be a variable position. The third position may be an end position, e.g. a position in which the activation member cannot further be moved in the delivery direction. When the activation member is moved by the second distance, and in particular from the second position towards the third position, the interaction members may mechanically cooperate with one another. Accordingly, when the activation member was moved by a certain distance (i.e. the first distance), the interaction members are brought into mechanical cooperation, in particular in direct mechanical contact, for generating friction between the interaction members.

According to one embodiment, the assembly is configured such that the amount of friction between the interaction members increases when the activation member is moved from the second position towards the third position. Accordingly, the more the user pushes onto the activation member, the greater the friction between the interaction members. In other words, the further the user pushes the activation member in the delivery direction, the greater the friction between the interaction members and, thus, the slower the relative rotational speed. Accordingly, the user can easily control the relative speed of the interaction members and, thus, the injection speed. Hence, provision of an easily working and user friendly device is facilitated.

According to one embodiment, the interaction members are free from mechanical cooperation during a dose setting operation of the assembly. Thus, the interaction members do not hamper a dose setting operation. In particular, no friction may be generated between the interaction members during dose setting.

According to one embodiment, the assembly further comprises a drive member. The drive member may be a drive shaft. The drive member may be adapted and arranged to be rotated during a dose setting operation of the assembly. The drive member may be adapted and arranged to be rotated during a dose delivery operation of the assembly. The first interaction member may be connected to the drive member. Alternatively, the first interaction member may be integrally formed with the drive member. By means of the first interaction member being connected to or being part of the drive member, rotational movement of the drive member is easily transferred to the first interaction member during dose delivery. Accordingly, the first interaction member may be rotated with respect to the second interaction member during dose delivery. Further components necessary for achieving a reduced injection speed of the assembly, which would make the assembly more complicated, are not needed in this way.

According to one embodiment, the assembly is configured such that movement of the activation member in the delivery direction causes movement of the drive member in the delivery direction. The drive member may move axially during dose delivery due to mechanical cooperation with the activation member. The drive member may be axially displaceable during a dose setting operation of the assembly. The drive member may be axially displaceable during a dose delivery operation of the assembly. By means of axial movement of the drive member in the delivery direction, relative axial movement of the interaction members may be achieved. In particular, the first interaction member may be axially moveable with respect to the second interaction member.

According to one embodiment, the assembly further comprises a dose setting member. The dose setting member may be shaped sleeve like. The dose setting member may be adapted and arranged to be rotated during a dose setting operation of the assembly. For example, the dose setting member may mechanically cooperate with the drive member during dose setting for being rotated. The dose setting member may be prevented from rotational movement during a dose delivery operation. For example, the dose setting member may be free from mechanical cooperation with the drive member during dose delivery. Thus, rotation of the dose setting member during dose delivery may be prevented. The dose setting member may be prevented from axial movement during dose setting and during dose delivery. The second interaction member may be connected to the dose setting member. Alternatively, the second interaction member may be integrally formed with the dose setting member. In other words, the second interaction member may be part of the dose setting member. By means of connecting the second interaction member to the dose setting member or, alternatively, forming the second interaction member and the dose setting member integrally, further components necessary for achieving a reduced injection speed of the assembly, which would make the assembly more complicated, are not needed.

According to one embodiment, the assembly further comprises a piston rod. The piston rod may be adapted and arranged to be moved in the delivery direction for dispensing a dose of a drug from the device.

The term "drug", as used herein, preferably means a pharmaceutical formulation containing at least one pharmaceutically active compound, wherein in one embodiment the pharmaceutically active compound has a molecular weight up to 1500 Da and/or is a peptide, a proteine, a polysaccharide, a vaccine, a DNA, a RNA, an enzyme, an antibody or a fragment thereof, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exendin-3 or exendin-4 or an analogue or derivative of exendin-3 or exendin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des (B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-Y-glutamyl)-des(B30) human insulin; B29-N—(N-lithocholyl-Y-glutamyl)-des(B30) human insulin; B29-

N-(ω-carboxyheptadecanoyl)-des(B30) human insulin and B29-N-(ω-carboxyhepta-decanoyl) human insulin.

Exendin-4 for example means Exendin-4(1-39), a peptide of the sequence H His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser-NH2.

Exendin-4 derivatives are for example selected from the following list of compounds:
H-(Lys)4-des Pro36, des Pro37 Exendin-4(1-39)-NH2,
H-(Lys)5-des Pro36, des Pro37 Exendin-4(1-39)-NH2,
des Pro36 Exendin-4(1-39),
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39); or
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39),
wherein the group -Lys6-NH2 may be bound to the C-terminus of the Exendin-4 derivative;
or an Exendin-4 derivative of the sequence
des Pro36 Exendin-4(1-39)-Lys6-NH2 (AVE0010),
H-(Lys)6-des Pro36 [Asp28] Exendin-4(1-39)-Lys6-NH2,
des Asp28 Pro36, Pro37, Pro38Exendin-4(1-39)-NH2,
H-(Lys)6-des Pro36, Pro38 [Asp28] Exendin-4(1-39)-NH2,
H-Asn-(Glu)5des Pro36, Pro37, Pro38 [Asp28] Exendin-4(1-39)-NH2,
des Pro36, Pro37, Pro38 [Asp28] Exendin-4(1-39)-(Lys)6-NH2,
H-(Lys)6-des Pro36, Pro37, Pro38 [Asp28] Exendin-4(1-39)-(Lys)6-NH2,
H-Asn-(Glu)5-des Pro36, Pro37, Pro38 [Asp28] Exendin-4(1-39)-(Lys)6-NH2,
H-(Lys)6-des Pro36 [Trp(O2)25, Asp28] Exendin-4(1-39)-Lys6-NH2,
H-des Asp28 Pro36, Pro37, Pro38 [Trp(O2)25] Exendin-4(1-39)-NH2,
H-(Lys)6-des Pro36, Pro37, Pro38 [Trp(O2)25, Asp28] Exendin-4(1-39)-NH2,
H-Asn-(Glu)5-des Pro36, Pro37, Pro38 [Trp(O2)25, Asp28] Exendin-4(1-39)-NH2,
des Pro36, Pro37, Pro38 [Trp(O2)25, Asp28] Exendin-4(1-39)-(Lys)6-NH2,
H-(Lys)6-des Pro36, Pro37, Pro38 [Trp(O2)25, Asp28] Exendin-4(1-39)-(Lys)6-NH2,
H-Asn-(Glu)5-des Pro36, Pro37, Pro38 [Trp(O2)25, Asp28] Exendin-4(1-39)-(Lys)6-NH2,
H-(Lys)6-des Pro36 [Met(O)14, Asp28] Exendin-4(1-39)-Lys6-NH2,
des Met(O)14 Asp28 Pro36, Pro37, Pro38 Exendin-4(1-39)-NH2,
H-(Lys)6-desPro36, Pro37, Pro38 [Met(O)14, Asp28] Exendin-4(1-39)-NH2,
H-Asn-(Glu)5 Pro36, Pro37, Pro38 [Met(O)14, Asp28] Exendin-4(1-39)-NH2,
des Pro36, Pro37, Pro38 [Met(O)14, Asp28] Exendin-4(1-39)-(Lys)6-NH2,
H-(Lys)6-des Pro36, Pro37, Pro38 [Met(O)14, Asp28] Exendin-4(1-39)-(Lys)6-NH2,
H-Asn-(Glu)5 des Pro36, Pro37, Pro38 [Met(O)14, Asp28] Exendin-4(1-39)-(Lys)6-NH2,
H-Lys6-des Pro36 [Met(O)14, Trp(O2)25, Asp28] Exendin-4(1-39)-Lys6-NH2,
H-des Asp28 Pro36, Pro37, Pro38 [Met(O)14, Trp(O2)25] Exendin-4(1-39)-NH2,
H-(Lys)6-des Pro36, Pro37, Pro38 [Met(O)14, Asp28] Exendin-4(1-39)-NH2,
H-Asn-(Glu)5-des Pro36, Pro37, Pro38 [Met(O)14, Trp(O2)25, Asp28] Exendin-4(1-39)-NH2,
des Pro36, Pro37, Pro38 [Met(O)14, Trp(O2)25, Asp28] Exendin-4(1-39)-(Lys)6-NH2,
H-(Lys)6-des Pro36, Pro37, Pro38 [Met(O)14, Trp(O2)25, Asp28] Exendin-4(S1-39)-(Lys)6-NH2,
H-Asn-(Glu)5-des Pro36, Pro37, Pro38 [Met(O)14, Trp(O2)25, Asp28] Exendin-4(1-39)-(Lys)6-NH2;
or a pharmaceutically acceptable salt or solvate of any one of the afore-mentioned Exendin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Antibodies are globular plasma proteins (~150 kDa) that are also known as immunoglobulins which share a basic structure. As they have sugar chains added to amino acid residues, they are glycoproteins. The basic functional unit of each antibody is an immunoglobulin (Ig) monomer (containing only one Ig unit); secreted antibodies can also be dimeric with two Ig units as with IgA, tetrameric with four Ig units like teleost fish IgM, or pentameric with five Ig units, like mammalian IgM.

The Ig monomer is a "Y"-shaped molecule that consists of four polypeptide chains; two identical heavy chains and two identical light chains connected by disulfide bonds between cysteine residues. Each heavy chain is about 440 amino acids long; each light chain is about 220 amino acids long. Heavy and light chains each contain intrachain disulfide bonds which stabilize their folding. Each chain is composed of structural domains called Ig domains. These domains contain about 70-110 amino acids and are classified into different categories (for example, variable or V, and constant or C) according to their size and function. They have a characteristic immunoglobulin fold in which two β sheets create a "sandwich" shape, held together by interactions between conserved cysteines and other charged amino acids.

There are five types of mammalian Ig heavy chain denoted by α, δ, ε, γ, and μ. The type of heavy chain present defines the isotype of antibody; these chains are found in IgA, IgD, IgE, IgG, and IgM antibodies, respectively.

Distinct heavy chains differ in size and composition; α and γ contain approximately 450 amino acids and δ approximately 500 amino acids, while μ and ε have approximately 550 amino acids. Each heavy chain has two regions, the constant region (CH) and the variable region (VH). In one species, the constant region is essentially identical in all antibodies of the same isotype, but differs in antibodies of different isotypes. Heavy chains γ, α and δ have a constant region composed of three tandem Ig domains, and a hinge region for added flexibility; heavy chains μ and ε have a constant region composed of four immunoglobulin domains. The variable region of the heavy chain differs in antibodies produced by different B cells, but is the same for all antibodies produced by a single B cell or B cell clone. The variable region of each heavy chain is approximately 110 amino acids long and is composed of a single Ig domain.

In mammals, there are two types of immunoglobulin light chain denoted by λ and κ. A light chain has two successive domains: one constant domain (CL) and one variable domain (VL). The approximate length of a light chain is 211 to 217 amino acids. Each antibody contains two light chains that are always identical; only one type of light chain, κ or λ, is present per antibody in mammals.

Although the general structure of all antibodies is very similar, the unique property of a given antibody is determined by the variable (V) regions, as detailed above. More specifically, variable loops, three each the light (VL) and three on the heavy (VH) chain, are responsible for binding to the antigen, i.e. for its antigen specificity. These loops are referred to as the Complementarity Determining Regions (CDRs). Because CDRs from both VH and VL domains contribute to the antigen-binding site, it is the combination of the heavy and the light chains, and not either alone, that determines the final antigen specificity.

An "antibody fragment" contains at least one antigen binding fragment as defined above, and exhibits essentially the same function and specificity as the complete antibody of which the fragment is derived from. Limited proteolytic digestion with papain cleaves the Ig prototype into three fragments. Two identical amino terminal fragments, each containing one entire L chain and about half an H chain, are the antigen binding fragments (Fab). The third fragment, similar in size but containing the carboxyl terminal half of both heavy chains with their interchain disulfide bond, is the crystalizable fragment (Fc). The Fc contains carbohydrates, complement-binding, and FcR-binding sites. Limited pepsin digestion yields a single F(ab')2 fragment containing both Fab pieces and the hinge region, including the H—H interchain disulfide bond. F(ab')2 is divalent for antigen binding. The disulfide bond of F(ab')2 may be cleaved in order to obtain Fab'. Moreover, the variable regions of the heavy and light chains can be fused together to form a single chain variable fragment (scFv).

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1 C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

The piston rod may be rotatable and axially moveable in the delivery direction during a dose delivery operation. However, the piston rod may be prevented from movement during a dose setting operation. The assembly may further comprise an energy storing member. The energy storing member may be a spring member, e.g. a torsion spring. The energy storing member may be adapted and arranged to store energy. Energy may be stored during a dose setting operation. The energy storing member may be adapted and arranged to cause movement of the piston rod in the delivery direction. When the activation member is operated, the piston rod may be driven due to the energy stored in the energy storing member for delivering the dose. In particular, the activation member may be configured to release the energy stored in the energy storing member. The amount of friction generated between the interaction members may control a speed of movement of the piston rod during the dose delivery operation. i.e. the injection speed. Accordingly, by controlling the speed of relative rotational movement of the interaction members, the injection speed of the assembly is controllable and, in particular, reducable.

According to one embodiment, the assembly is configured such that movement of the activation member from the first position towards the second position releases the energy stored in the energy storing member for causing movement of the piston rod in the delivery direction. Accordingly, the interaction members may be brought in contact after releasing or directly in the moment when releasing the energy stored in the energy storing member. In this way, the injection speed can be effectively controlled.

According to one embodiment, the assembly further comprises a locking member. The locking member may be a clutch member. The assembly may further comprise a housing. Movement of the locking member with respect to the housing may be prevented during a dose setting operation of the assembly due to mechanical cooperation of the locking member with the housing. In particular, during a dose setting operation, the housing and the locking member may be releasably connected. Accordingly, the locking member may be prevented from rotation with respect to the housing during dose setting. The assembly may be configured such that movement of the activation member from the first position towards the second position disengages the locking member and the housing such that the locking member is rotatable with respect to the housing for releasing an energy stored in the energy storing member. Accordingly, during a dose delivery operation, the housing and the locking member may no longer be connected. Energy is released to drive the piston rod automatically in the delivery direction.

According to one embodiment, the first interaction member comprises at least one wedge. The first interaction member may comprise a circular wedge. Alternatively, the first interaction member may comprise a partly circular wedge. In this case, the first interaction member may comprise a plurality of wedges, e.g. two, three, four or more wedges. The wedge or the wedges may be arranged around an outer surface of the drive member. The wedge or the wedges may be arranged circumferentially around the drive member. The wedge or the wedges may be arranged in an end section of the drive member. The second interaction member may comprise a counter surface, e.g. an inclined surface. By means of mechanical cooperation of these interaction members, the relative rotational speed of the interaction members and, thus, the injection speed can be effectively controlled. Thus, provision of a device with high user comfort is facilitated.

A further aspect relates to a drug delivery device. The device may comprise the previously mentioned assembly. In particular, the assembly may be implemented in the device. The assembly may be implemented as a drive mechanism of the device. The device may further comprise a cartridge for holding a plurality of doses of the drug. The device may be an automatic device. By means of the assembly, the user can control the relative rotational speed of the interaction members during dose delivery. Accordingly, the user can control the speed of movement of the piston rod. In particular, he can adjust the speed to his individual needs. Thus, a very user friendly device is provided.

Of course, features described above in connection with different aspects and embodiments may be combined with each other and with features described below.

Further features and refinements become apparent from the following description of the exemplary embodiments in connection with the accompanying figures.

Like elements, elements of the same kind and identically acting elements may be provided with the same reference numerals in the figures.

Figure 1:
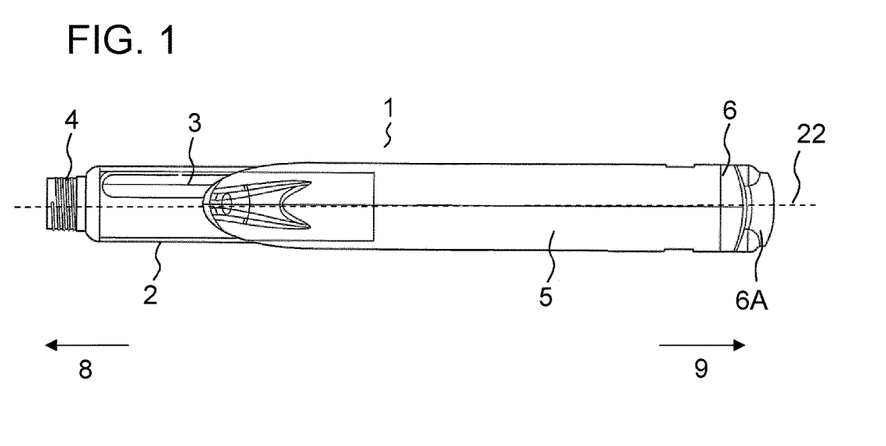
FIG. 1 schematically shows a three-dimensional view of a drug delivery device.

In FIG. 1 a drug delivery device 1 is shown. The drug delivery device 1 comprises a housing 5. The housing 5 is adapted and arranged for protecting components of the device 1 arranged within the housing 5 from environmental influences. The drug delivery device 1 and the housing 5 have a distal end 8 and a proximal end 9. The term "distal end" designates that end of the drug delivery device 1 or a component thereof which is or is to be arranged closest to a dispensing end of the drug delivery device 1. The term "proximal end" designates that end of the device 1 or a component thereof which is or is to be arranged furthest away from the dispensing end of the device 1. The distal end 8 and the proximal end 9 are spaced apart from one another in the direction of an axis 22. The axis 22 may be the longitudinal axis or rotational axis of the device 1.

The drug delivery device 1 comprises a cartridge holder 2. The cartridge holder 2 comprises a cartridge 3. The cartridge 3 contains a drug 10, preferably a plurality of doses of the drug 10. The cartridge 3 is retained within the cartridge holder 2. The cartridge holder 2 stabilizes the position of the cartridge 3 mechanically. The cartridge holder 2 is connectable, e.g. by a threaded engagement or by a bayonet coupling, to the housing 5. The cartridge holder 2 and the housing 5 may be releasably or non-releasably connected to one another. In an alternative embodiment, the cartridge 3 may be directly connected to the housing 5. In this case, the cartridge holder 2 may be redundant.

The drug delivery device 1 may be a pen-type device, in particular a pen-type injector. The device 1 may be a re-usable device, which means that the cartridge 3 can be replaced, in particular during a reset operation, by a replacement cartridge for dispensing a plurality of doses from the replacement cartridge. Alternatively, the device 1 may be a disposable device. The device 1 can be configured to dispense variable doses of the drug 10. Alternatively, the device 1 may be a fixed dose device. The device 1 may be an auto-injection device. This means that a dose delivery operation of the device 1 may be initiated by the user by pressing an actuation member 6A, wherein upon pressing the actuation member 6A an energy stored in the device 1 is released for dispensing a dose of the drug 10. The auto-injector may be configured to substantially expel the entire content from the cartridge 3. Alternatively, the auto-injector may comprise a dose setting member 6 configured to determine the amount of drug 10 to be expelled.

A bung 11 (see FIG. 2) is slideably retained within the cartridge 3. The bung 11 seals the cartridge 3 proximally. Movement of the bung 11 in the distal direction with respect to the cartridge 3 causes the drug 10 to be dispensed from the cartridge 3. A needle assembly (not explicitly shown in the Figures) can be arranged at the distal end section of the cartridge holder 2, e.g. by means of an engagement means 4, e.g. a thread.

Figure 2:
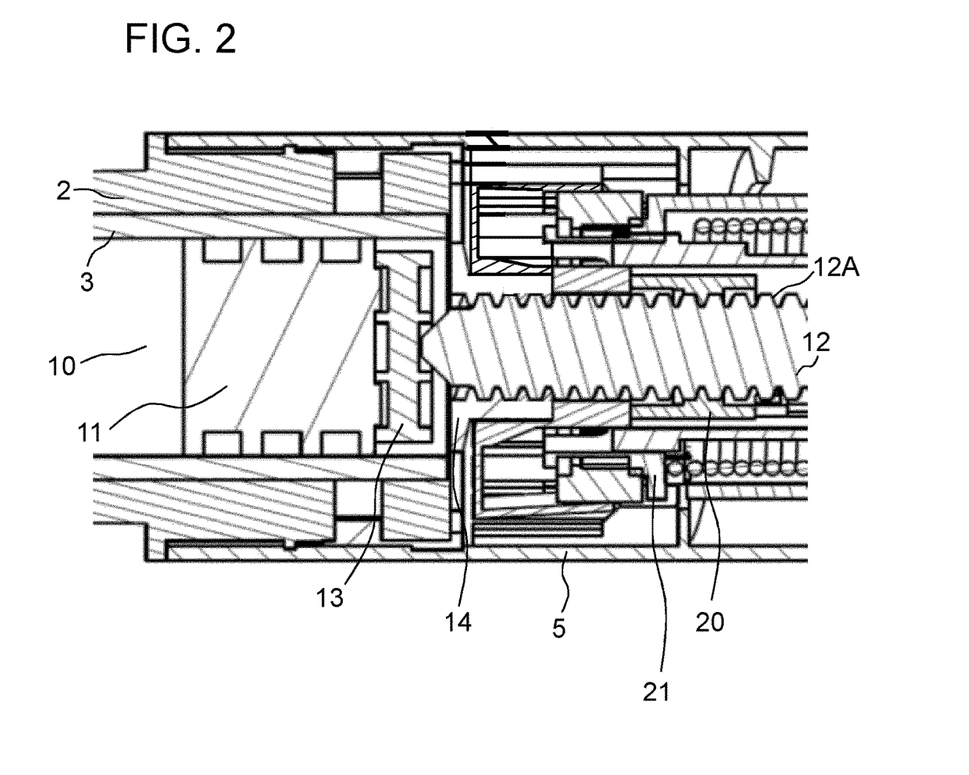
FIG. 2 schematically shows a sectional side view of a part of the drug delivery device of FIG. 1, FIG. 3 schematically shows a sectional side view of a part of the drug delivery device of FIG. 1, FIG. 4 schematically shows a sectional side view of a part of the drug delivery device of FIG. 1.
Figure 3:
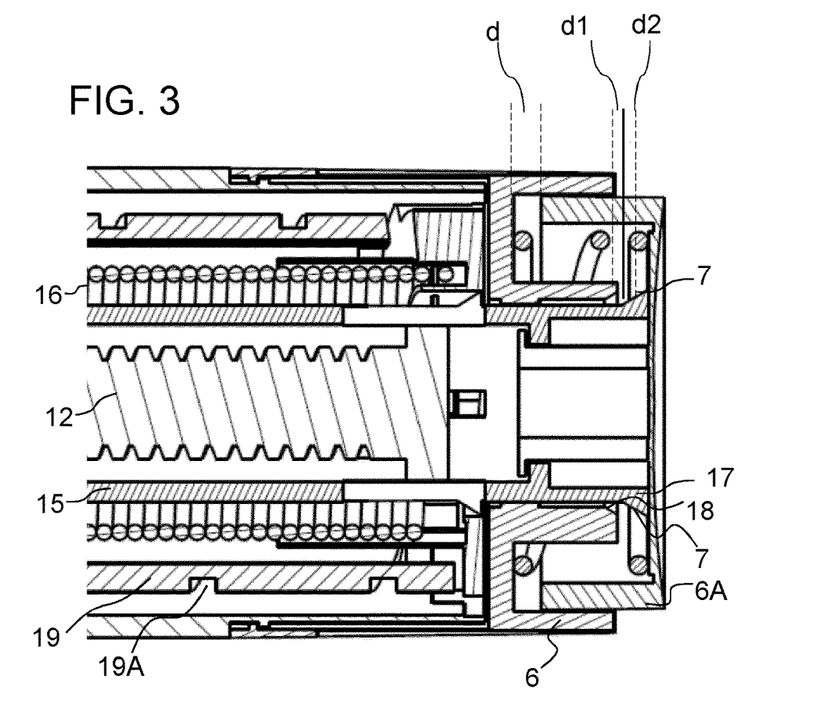
Figure 4:
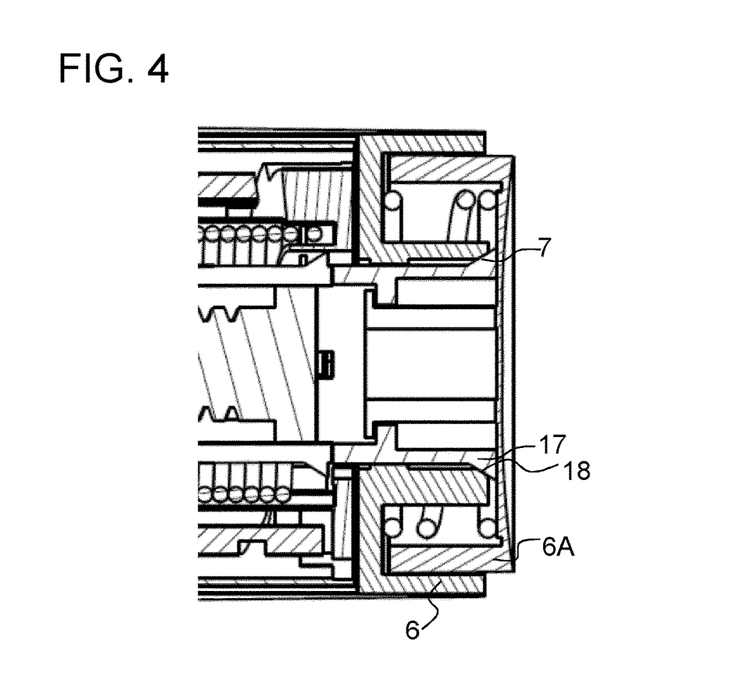

FIGS. 2 to 4 show a sectional side view of a part of the drug delivery device of FIG. 1.

The device 1 comprises a piston rod 12. The piston rod 12 is configured to be moved in a distal direction in order to dispense a dose of the drug 10. The distal direction may be a delivery direction. The piston rod 12 is moved along the longitudinal axis 22 of the device 1. The longitudinal axis 22 is, thus, the axis of movement of the piston rod 12. The piston rod 12 is configured to move the bung 11 arranged in the cartridge 3 towards the dispensing end of the drug delivery device 1. The piston rod 12 comprises a bearing member 13 which is in contact with the bung 11. The piston rod 12 is configured as a lead screw. The piston rod 12 comprises an outer thread 12A. The thread 12A is arranged along an outer surface of the piston rod 12.

The device 1 may further comprise a drive feature 20. The drive feature 20 may be a nut member, e.g. a spline nut. The drive feature 20 is engaged with the piston rod 12. In particular, the drive feature 20 comprises splines, which are engaged with axial grooves of the piston rod 12. Thus, the drive feature 20 is rotationally fixed but axially moveable with respect to the piston rod 12. The drive feature 20 and, thus, the piston rod 12 may be rotatable during a dose delivery operation. In an alternative embodiment, the drive feature 20 and the piston rod 12 may be prevented from rotational movement with respect to the housing 5.

The device 1 further comprises a guide member 14. The piston rod 12 is guided through the guide member 14. The guide member 14 is arranged around the piston rod 12. The guide member 14 may be a nut member. The guide member 14 is preferably configured as a thread nut. The guide member 14 is in threaded engagement, preferably in permanent threaded engagement, with the piston rod 12. For this purpose, the guide member 14 comprises an inner thread which is in engagement with the outer thread 12A of the piston rod 12. The guide member 14 is secured against movement with respect to the housing 5. When the drive feature 20 rotates during a dose delivery operation, the piston rod 12 is also rotated. Due to the threaded engagement between the piston rod 12 and the guide member 14, rotation of the piston rod 12 causes the piston rod 12 to move in the distal direction. Thereby, the bung 11 is moved in the distal direction for dispensing a dose of the drug 10.

Prior to dose delivery, the required dose of drug 10 is set by means of a dose setting mechanism. Common designs of dose setting mechanisms comprise a number of tubular or sleeve-like members such as a dose setting sleeve, a dose indicating sleeve, a drive sleeve and/or a ratchet sleeve. Such sleeves are often accommodated within and connected to each other.

The device 1 and, in particular the dose setting mechanism, comprises a dose setting member 6. The dose setting member 6 may be shaped sleeve-like. The dose setting member 6 is axially fixed but rotationally moveable with respect to the housing 5. The dose setting member 6 is configured for setting a dose of the drug 10. The dose setting member 6 is rotatable with respect to the housing 5 for setting a dose of the drug 10. The dose setting member 6 can be rotated by a user. The dose setting member 6 is prevented from rotation with respect to the housing 5 during a dose delivery operation due to mechanical cooperation with the housing 5.

The device 1 further comprises a drive member 15. The drive member 15 may comprise a drive shaft. The drive member 15 may be arranged around the piston rod 12. The drive member 15 is connected to the dose setting member 6 for setting a dose of the drug 10. In particular, the drive member 15 may be rotationally fixed to the dose setting member 6 during the dose setting operation due to a splined connection. Thus, by rotating the dose setting member 6 during a dose setting operation, the drive member 15 is also rotated. The drive member 15 may be disconnected from the dose setting member 6 for delivery of the set dose, which is explained later on in detail. The drive member 15 is rotatable during dose delivery.

The device 1 further comprises a rotation member 19. The rotation member 19 is shaped sleeve-like. The rotation member 19 is rotatable with respect to the housing 5. The rotation member 19 is arranged concentrically around the drive member 15. The rotation member 19 may be fixed to the drive member 15, e.g. by a snap-fit connection. The rotation member 19 is axially fixed with respect to the drive member 15. Rotation of the drive member 15 during a dose setting operation causes rotation of the rotation member 19. For this purpose the rotation member comprises a thread 19A which may engage an inner thread of the housing 5 (not explicitly shown). The direction in which the drive member 15 and the rotation member 19 are rotated during dose setting, i.e. a first rotational direction, may be a clockwise direction. When the rotation member 19 is rotated during dose setting, the rotation member 19 moves in the proximal direction with respect to the housing 5. The direction in which the drive member 15 and the rotation member 19 are rotated during dose delivery, i.e. a second rotational direction, may be an anti-clockwise direction.

To improve the user comfort the device 1 comprises a power assistance, in particular an energy storing member 16. The energy storing member 16 may be a coil spring. The energy storing member 16 may be a torsion spring. When the dose setting member 6 and, thus, the rotation member 19 is rotated during dose setting, the energy storing member 16 is compressed, such that energy is stored in the energy storing member 16. Thereby, a clicking noise is produced e.g. by a single ratchet on a ratchet sleeve (not explicitly shown in the Figures).

The device 1 further comprises a locking member 21 (see FIG. 2). The locking member 21 may be a clutch member. The locking member 21 is fixed with respect to the housing 5 during the setting of a dose. In particular, the locking member 21 and the housing 5 may comprise corresponding engagement means (not explicitly shown in the Figures), e.g. splines. The corresponding engagement means may be engaged during the setting of a dose. The rotation member 19 is coupled to the locking member 21.

The locking member 21 is configured to inhibit an unintended rotation of the rotation member 19 during the setting of a dose. Thereby, the locking member 21 inhibits a relaxation of the energy storing member 16. For this purpose, the rotation member 19 may be engaged with the locking member 21 by a toothed connection (not explicitly shown in the Figures) such that rotation of the rotation member 19 in the first rotational direction is allowed during the dose setting operation and such that rotation of the rotation member 19 in a direction opposite to the first rotational direction, i.e. in the second rotational direction, is prevented during the dose setting operation. Alternatively, the rotation member 19 may comprise a ratchet mechanism (not explicitly shown in the Figures). The rotation member 19 may be coupled to the locking member 21 by means of the ratchet mechanism. The ratchet mechanism may comprise a ratchet arm, for example. The ratchet arm may be engaged with the locking member 21 such that an unintended rotation of the rotation member 19 in the second rotational direction during dose setting may be inhibited. However, the ratchet mechanism allows a rotation of the rotation member 19 in the first rotational direction with respect to the locking member 21 for setting a dose, as described above.

The device 1 further comprises the previously mentioned actuation member 6A. The actuation member 6A is axially moveable with respect to the housing 5. The actuation member 6A is prevented from rotational movement with respect to the housing 5. In order to dispense a dose, the actuation member 6A is operated by a user. The actuation member 6A may comprise a button. When the actuation member 6A is axially moved in the delivery direction, the energy storing member 16 is released and drives the piston rod 12 to deliver a dose of the drug 10 from the cartridge 3. The user of the device 1 does, thus, not have to provide the force for dispense.

In particular, when the actuation member 6A is actuated, e.g. moved in the distal or delivery direction, the drive member 15 is also moved in the distal direction. Thereby, the drive member 15 is moved out of engagement with the dose setting member 6. When the drive member 15 is moved in the distal direction, the rotation member 19 and the locking member 21 are also moved in the distal direction. Thereby, the locking member 21 is disengaged from its engagement with the housing 5. In particular, the locking member 21 is allowed to rotate with respect to the housing 5 when the actuation member 6A is actuated by a user. When the locking member 21 is allowed to rotate, the rotation member 19 and the drive member 15 are allowed to rotate, as well. When the locking member 21 is enabled to rotate with respect to the housing 5, the energy which is stored in the energy storing member 16 is released causing a rotation of the drive member 15 and, thus, of the rotation member 19 in the distal direction. Rotation of the rotation member 19 causes rotation of the drive feature 20 and, thus, rotational movement of the piston rod 12 in the distal direction for dispensing a dose of the drug 10.

In conventional drug delivery devices, the user has no control over the speed with which the piston rod 12 is moved during the dose delivery operation, i.e. the injection speed. In particular, when the above mentioned locking member 21 is released, the injection speed is independent from the pressed actuation member 6A. However, it is desirable for the user to control the injection speed, e.g. to reduce the pain when the drug 10 is injected into the tissue.

For this purpose, the device 1 comprises a first interaction member 17 (see FIGS. 3 and 4). The device 1 further comprises a second interaction member 18 (see FIGS. 3 and 4). The first and second interaction members 17, 18 are configured to mechanically cooperate with one another during a dose delivery operation. However, the first and second interaction members 17, 18 are free from mechanical cooperation during a dose setting operation. The first and the second interaction members 17, 18 are rotatable with respect to one another. The first and the second interaction members 17, 18 are axially moveable with respect to one another.

The first interaction member 17 is rotatable with respect to the housing 5 and with respect to the second interacton member 18 during a dose delivery operation. The first interaction member 17 may be rotatable with respect to the housing 5 during a dose setting operation, as well. The first interaction member 17 may be connected to the drive member 15, for example. Alternatively, the first interaction member 17 and the drive member 15 may be formed unitarily. In other words, the first interaction member 17 may be part of the drive member 15. The first interaction member 17 is arranged in a proximal end section of the drive member 15. The first interaction member 17 may be arranged circumferentially around the proximal end section of the drive member 15. In an alternative embodiment (not explicitly shown) the first interaction member 17 may be connected to or may be part of any other member of the device 1 which is rotatable and axially moveable during a dose delivery operation of the device.

The first interaction member 17 comprises an inclined surface 7. In particular, the first interaction member 17 comprises a surface 7 which encloses an angle with the longitudinal axis 22. The first interaction member 17 may comprise at least one wedge. The wedge may be a circular or partly circular wedge. Alternatively, the first interaction member 17 may comprise a plurality of wedges, e.g. two, three, four or more wedges. The wedge or the wedges may be arranged around the proximal end section of the drive member 15.

The second interaction member 18 is prevented from rotation with respect to the housing 5 during a dose delivery operation. However, the second interaction member 18 may be rotatable during a dose setting operation. In other words, at least during dose delivery, the first interaction member 17 is rotatable with respect to the second interaction member 18. The second interaction member 18 may be connected to the dose setting member 6, for example. Alternatively, the second interaction member 16 and the dose setting member 6 may be formed unitarily. In other words, the second interaction member 18 may be part of the dose setting member 6. The second interaction member 18 is arranged in a proximal end section of the dose setting member 6. The second interaction member 18 is arranged at an outer surface of the dose setting member 6 which faces the first interaction member 17. In an alternative embodiment (not explicitly shown) the second interaction member 18 may be connected to or may be part of any other member of the device 1 which is non-rotatable and not axially moveable during a dose delivery operation of the device and which faces a proximal end section of that component comprising the first interaction member 17.

The second interaction member 18 comprises an inclined surface. In particular, the second interaction member 18 comprises a surface which encloses an angle with the longitudinal axis 22. The inclined surface may be that surface of the second interaction member 18 which faces the first interaction member 17.

The interaction members 17, 18 are configured to mechanically cooperate during dose delivery such that a friction is generated between the interaction members 17, 18. The amount of friction influences a rotational speed of the first interaction member 17. In other words, the amount of friction influences a relative rotational speed of the interaction members 17, 18 during dose delivery. The greater the friction between the interaction members 17, 18 the smaller the rotational speed. The smaller the relative rotational speed, the smaller the rotational speed of the drive member 15 and of the rotation member 19 during dose delivery. As movement of the rotation member 19 during dose delivery is converted into movement of the piston rod 12, a speed of movement of the piston rod 12 is influenced and, in particular, decreased due to mechanical cooperation of the interaction members 17, 18.

For bringing the interaction members 17, 18 into mechanical cooperation, a dose delivery operation must be initiated by the user. For this purpose, the user pushes the activation member 6A distally. Upon distal movement of the actuation member 16, the drive member 15 and, thus, the first interaction member 17 is moved distally as well. The first interaction member 17 is moved distally towards the second interaction member 18. However, the interaction members 17, 18 are not at once in mechanical contact when the actuation member 6A is moved distally. Rather, the actuation member 6A and, thus, the drive member 15 must be moved by a certain distance for bringing the interaction members 17, 18 into mechanical contact.

In particular, the activation member 6A is moved by a first distance d1 (see FIG. 3) from a first position into a second position. The first position may be a starting position, i.e. the position in which the activation member 6A is arranged with respect to the housing 5 before the user pushes onto the actuation member 6A. The second position may be an intermediate position. The second position may be that position of the actuation member 6A with respect to the housing 5 in which the interaction members 17, 18 start to mechanically cooperate with one another. The distance d1 the actuation member 6A is moved between the first and the second position may be one half of a total distance d the actuation member 6A is moveable for delivering a dose of the drug 10. Alternatively, the distance d1 the actuation member 6A is moved between the first and the second position may be one third of the total distance d the actuation member 6A is moved for delivering a dose of the drug 10, for example. The first distance d1 is smaller than the total distance d. The first distance d1 may, for example, depend on the angle the surface 7 of the first interaction member 17 encloses with the longitudinal axis 22. The greater the angle, the smaller may be the first distance d1. The first distance d1 is thus, a variable distance and depends on the structure of the components of the device. Accordingly, the second position is a variable position.

When the actuation member 6A is moved from the first position towards the second position, the drive member 15 is moved distally and, thus, the locking member 21 is disengaged from the housing 5. Accordingly, the energy storing member 16 can relax resulting in a rotational movement of the drive member 15 and the rotation member 19 as described above.

When the actuation member 6A is in the second position the first and the second interaction member 17, 18 start to mechanically cooperate. Accordingly, the interaction members 17, 18 mechanically cooperate directly in the moment or after the moment of disengaging the locking member 21 from the housing 5. As the first interaction member 17 is rotatable with respect to the second interaction member 18, friction is generated between the interaction members 17, 18 when the interaction members 17, 18 are brought in contact. The amount of friction depends on the relative axial position of the interaction members 17, 18 and, thus, on a degree of mechanical cooperation between the interaction members 17, 18. The amount of friction depends on the axial position of the activation member 6A.

When the actuation member 6A is arranged in the second position it has not yet reached a final position, i.e. a third position with respect to the housing 5. The final or third position may be that position in which the actuation member 6A is arranged at the end of the delivery operation. The activation member 6A is movable between the second position and the third position by a second distance d2 (see FIG. 3). The second distance d2 by which the actuation member 6A is moved between the second and the third position may be one half of the total distance d the actuation member 6A is moveable for delivering a dose of the drug 10. The second distance d2 may be equal to the first distance d1. Alternatively, the second distance d2 may be greater than the first distance d1. The sum of the first distance d1 and the second distance d2 is equal to the total distance d.

In the third position, the actuation member 6A may abut with a proximal end face of the dose setting member 6 (see FIG. 4). Thus, the dose setting member 6 may limit the distal movement of the actuation member 6A. Alternatively, the interaction members 17, 18 may limit the distal movement of the actuation member 6A during dose delivery. The second distance d2 may, for example, depend on the angle the surface 7 of the first interaction member 17 encloses with the longitudinal axis 22. If the angle exceeds a predetermined angle, e.g. 45 degree, distal movement of the actuation member 6A may be stopped due to mechanical cooperation of the interaction members 17, 18 instead of due to abutment with the dose setting member 6. Thus, the second distance d2 may be a variable distance. The third position may be a variable position.

Upon further movement of the actuation member 6A from the second position towards the third position, a contact area between the interaction members 17, 18 increases. Accordingly, the amount of friction between the interaction members 17, 18 increases. Thus, the more the user presses onto the activation member 6A, the more friction will be generated and, therefore, the smaller may be the relative rotational speed of the interaction members 17, 18. When the relative rotational speed of the interaction members 17, 18 is slowed down, the speed of movement of the piston rod 12 is slowed down, as well. Thus, by controlling the distance by which the actuation member 6A is moved distally during dose delivery, the user can control the injection speed of the device 1.

Other implementations are within the scope of the following claims. Elements of different implementations may be combined to form implementations not specifically described herein.

REFERENCE NUMERALS

1 Drug delivery device
2 Cartridge holder
3 Cartridge
4 Engagement means
5 Housing
6A Activation member
6 Dose setting member
7 Inclined surface
8 Distal end
9 Proximal end
10 Drug
11 Bung
12 Piston rod
13 Bearing member
14 Guide member
15 Drive member
16 Energy storing member
17 First interaction member
18 Second interaction member
19 Rotation member
19A Thread
20 Drive feature
21 Locking member
22 Longitudinal axis
d Distance
d1 First distance
d2 Second distance

The invention claimed is:

1. An assembly for a drug delivery device comprising:
an activation member adapted to be axially moved in a delivery direction for triggering a dose delivery operation of the assembly;
a first interaction member; and
a second interaction member, the first and second interaction members are adapted to mechanically cooperate with one another during a dose delivery operation of the assembly and to be rotated with respect to one another during the dose delivery operation, wherein the assembly is configured such that movement of the activation member in the delivery direction brings the interaction members into mechanical contact for generating friction between the interaction members, wherein the friction controls a relative rotational speed of the interaction members during the dose delivery operation,
wherein the activation member is configured to be pushed in the delivery direction by a user, and the assembly is configured such that an amount of pressure exerted onto the activation member determines an amount of friction generated between the interaction members, and
wherein the more the activation member is pushed in the delivery direction the more friction is generated between the first and second interaction members.

2. The assembly according to claim 1, wherein the activation member is adapted to be moved in the delivery direction by a first distance from a first position into a second position, wherein when the activation member is moved by the first distance, the interaction members are free from mechanical cooperation.

3. The assembly according to claim 2, wherein the activation member is adapted to be moved in the delivery direction by a second distance from the second position into a third position, wherein when the activation member is moved by the second distance, the interaction members mechanically cooperate with one another.

4. The assembly according to claim 3, wherein the assembly is configured such that friction between the interaction members increases when the activation member is moved from the second position towards the third position.

5. The assembly according to claim 1, wherein the interaction members are free from mechanical cooperation during a dose setting operation of the assembly.

6. The assembly according to claim 1, further comprising a drive member adapted to be rotated during a dose setting and during a dose delivery operation of the assembly, wherein the first interaction member is connected to or is integrally formed with the drive member.

7. The assembly according to claim 6, wherein the assembly is configured such that axial movement of the activation member in the delivery direction causes axial movement of the drive member in the delivery direction.

8. The assembly according to claim 1, further comprising a dose setting member adapted to be rotated during a dose setting operation of the assembly, wherein the dose setting member is prevented from rotational movement during the dose delivery operation, and wherein the second interaction member is connected to or is integrally formed with the dose setting member.

9. The assembly according to claim 1 further comprising:
a piston rod adapted to be moved in the delivery direction for dispensing a dose of a drug from the device, and
an energy storing member adapted to store energy and to cause movement of the piston rod in the delivery direction,
wherein the friction generated between the interaction members controls a speed of movement of the piston rod during the dose delivery operation.

10. The assembly according to claim 9, wherein the assembly is configured such that movement of the activation member from a first position towards a second position releases the energy stored in the energy storing member for causing movement of the piston rod in the delivery direction.

11. The assembly according to claim 9, further comprising a locking member and a housing, wherein movement of the locking member with respect to the housing is prevented during a dose setting operation of the assembly by a mechanical cooperation with the housing, and wherein the assembly is configured such that movement of the activation member from a first position towards a second position disengages the locking member and the housing such that the locking member is configured to rotate with respect to the housing and release energy stored in the energy storing member.

12. The assembly according to claim 1, wherein the first interaction member comprises at least one wedge.

13. The assembly according to claim 1, wherein the amount of friction depends on the axial position of the activation member.

14. A drug delivery device comprising:
an assembly comprising:
an activation member adapted to be axially moved in a delivery direction for triggering a dose delivery operation of the assembly,
a first interaction member and
a second interaction member, the first and second interaction members are adapted to mechanically cooperate with one another during a dose delivery operation of the assembly and to be rotated with respect to one another during the dose delivery operation, wherein the assembly is configured such that movement of the activation member in the delivery direction brings the interaction members into mechanical contact for generating friction between the interaction members, wherein the friction controls a relative rotational speed of the interaction members during a dose delivery operation; and
a housing containing a cartridge, the housing being configured to hold a plurality of doses of a drug,
wherein the activation member is configured to be pushed in the delivery direction by a user, and the assembly is configured such that an amount of pressure exerted onto the activation member determines an amount of friction generated between the interaction members, and wherein the more the activation member is pushed in the delivery direction the more friction is generated between the first and second interaction members.

15. The drug delivery device of claim 14, wherein the drug contains a pharmaceutically active compound.

16. A method comprising:
pushing an activation member of a drug delivery device in a delivery direction thereby moving a first interaction member of the drug delivery device into frictional engagement with a second interaction member of the drug delivery device with a force and releasing energy from an energy storage member into a rotation member, the rotation member driving rotation of a piston rod and the piston rod expelling a dose of drug from the drug delivery device, wherein the friction engagement between the interaction members retards a speed of the piston rod; and
controlling the speed of the piston rod by adjusting the force applied to the first interaction member to define the degree of frictional engagement between the first and second interaction members, wherein an amount of pressure exerted onto the activation member determines an amount of friction generated between the interaction members, and
wherein the more the activation member is pushed in the delivery direction the more friction is generated between the first and second interaction members.

17. An assembly for a drug delivery device comprising:
an activation member adapted to be axially moved in a delivery direction for triggering a dose delivery operation of the assembly;
a first interaction member; and
a second interaction member, the first and second interaction members are adapted to mechanically cooperate with one another during a dose delivery operation of the assembly and to be rotated with respect to one another during the dose delivery operation, wherein the assembly is configured such that movement of the activation member in the delivery direction brings the interaction members into mechanical contact for generating friction between the interaction members, wherein the friction controls a relative rotational speed of the interaction members during the dose delivery operation, wherein the activation member is adapted to be moved in the delivery direction by a first distance from a first position into a second position, wherein when the activation member is moved by the first distance, the interaction members are free from mechanical cooperation.

18. The assembly according to claim 17, wherein the activation member is adapted to be moved in the delivery direction by a second distance from the second position into a third position, wherein when the activation member is moved by the second distance, the interaction members mechanically cooperate with one another.

19. The assembly according to claim 18, wherein the assembly is configured such that friction between the interaction members increases when the activation member is moved from the second position towards the third position.

20. A drug delivery device comprising:
an assembly comprising:
an activation member adapted to be axially moved in a delivery direction for triggering a dose delivery operation of the assembly,
a first interaction member and
a second interaction member, the first and second interaction members are adapted to mechanically cooperate with one another during a dose delivery operation of the assembly and to be rotated with respect to one another during the dose delivery operation, wherein the assembly is configured such that movement of the activation member in the delivery direction brings the interaction members into mechanical contact for generating friction between the interaction members, wherein the friction controls a relative rotational speed of the interaction members during a dose delivery operation; and a housing containing a cartridge, the housing being configured to hold a plurality of doses of a drug, wherein the activation member is adapted to be moved in the delivery direction by a first distance from a first position into a second position, wherein when the activation member is moved by the first distance, the interaction members are free from mechanical cooperation.

21. The drug delivery device of claim 20, wherein the drug contains a pharmaceutically active compound.

22. An assembly for a drug delivery device comprising:
an activation member adapted to be axially moved in a delivery direction for triggering a dose delivery operation of the assembly;
a first interaction member; and
a second interaction member, the first and second interaction members are adapted to mechanically cooperate with one another during a dose delivery operation of the assembly and to be rotated with respect to one another during the dose delivery operation, wherein the assembly is configured such that movement of the activation member in the delivery direction brings the interaction members into mechanical contact for generating friction between the interaction members, wherein the friction controls a relative rotational speed of the interaction members during the dose delivery operation, wherein the interaction members are free from mechanical cooperation during a dose setting operation of the assembly.

23. The assembly according to claim 22, further comprising a drive member adapted to be rotated during a dose setting and during a dose delivery operation of the assembly, wherein the first interaction member is connected to or is integrally formed with the drive member.

24. The assembly according to claim 22, further comprising a dose setting member adapted to be rotated during a dose setting operation of the assembly, wherein the dose setting member is prevented from rotational movement during the dose delivery operation, and wherein the second interaction member is connected to or is integrally formed with the dose setting member.

25. A drug delivery device comprising:
an assembly comprising:
an activation member adapted to be axially moved in a delivery direction for triggering a dose delivery operation of the assembly,
a first interaction member and
a second interaction member, the first and second interaction members are adapted to mechanically cooperate with one another during a dose delivery operation of the assembly and to be rotated with respect to one another during the dose delivery operation, wherein the assembly is configured such that movement of the activation member in the delivery direction brings the interaction members into mechanical contact for generating friction between the interaction members, wherein the friction controls a relative rotational speed of the interaction members during a dose delivery operation; and
a housing containing a cartridge, the housing being configured to hold a plurality of doses of a drug, wherein the interaction members are free from mechanical cooperation during a dose setting operation of the assembly.

26. The drug delivery device of claim 25, wherein the drug contains a pharmaceutically active compound.

* * * * *

UNITED STATES PATENT AND TRADEMARK OFFICE
CERTIFICATE OF CORRECTION

PATENT NO. : 10,159,801 B2
APPLICATION NO. : 15/105738
DATED : December 25, 2018
INVENTOR(S) : Michael Jugl, Axel Teucher and Marc Holtwick It is certified that error appears in the above-identified patent and that said Letters Patent is hereby corrected as shown below:

On the Title Page

Column 1, Line 2 under item (73) "Assignee", delete "Frankfult" and insert -- Frankfurt --

Signed and Sealed this
Seventh Day of January, 2020

Andrei Iancu
*Director of the United States Patent and Trademark Office*